United States Patent Office

Plant Pat. 1,914
Patented Feb. 23, 1960

1,914

ROSE PLANT

Gordon J. von Abrams, Portland, Oreg., assignor to Eldon Pinkeney Dering, doing business as Peterson & Dering, Scappoose, Oreg.

Application January 9, 1959, Serial No. 785,991

1 Claim. (Cl. 47—61)

The present invention relates to a new and distinct variety of rose plant of the hybrid tea class, which was originated by me by crossing the variety "Charles Mallerin" (Plant Patent No. 933) with an unnamed and unpatented seedling derived from a cross of "Charles Mallerin" × "Chrysler Imperial" (Plant Patent No. 1,167).

The primary objective of this breeding was to produce a new rose variety having a plant habit which overcomes the awkward growth habit of the seed parent "Charles Mallerin," combined with a more abundant flowering habit than that of the seed parent, and which produces flowers of a deep red color, with less tendency to discolor in hot weather or to fail to open in wet, cool weather. This objective was fully achieved with the attainment of all of these features, along with other desirable improvements, as evidenced by the following phenotypic characteristics which are outstanding in the new variety and which distinguish it from its parents, as well as from all other varieties of which I am aware:

(1) An upright, bushy, vigorous, medium tall (about 4 feet) plant habit;

(2) Abundant, large and well-distributed foliage of a deep green color;

(3) A continuous and quite floriferous flowering habit throughout the growing season, although sometimes starting later than many varieties;

(4) A habit of bearing flowers singly on long, strong stems;

(5) A unique combination of flower form and color which is distinct from any other rose in commerce known to me; and (6) A tendency for one or more axial buds to begin growth before the flower reaches senescence.

In comparison with its seed parent, "Charles Mallerin," the new variety, in achieving the aforementioned characteristics by way of improvement over this parent, has also achieved a more graceful plant habit; a more abundant flowering habit; a more desirable reaction of the flowers to hot, dry, wet and cool weather conditions; the buds are smaller; the flower is more open in form and has fewer petals; and the flower color is lighter, less black and of lesser chromatic value than the flowers of this parent.

As compared with its unnamed pollen parent, my new variety has a more upright plant habit; the foliage is darker and much less glossy; and the flowers are larger and of a darker color.

Asexual reproduction of the new variety by budding, as performed by me at Scappoose, Oregon, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson"), Robert Ridgway's Color Standards and Nomenclature (hereinafter abbreviated as "Ridgway"), and the Nickerson Color Fan (hereinafter abbreviated as "Nickerson"), except where general color terms of ordinary dictionary significance are obvious:

Type: Semi-hardy; medium tall; bush; outdoor; seedling; for cut flowers and for garden decoration.

Class: Hybrid tea.

Breeding: Seedling.

*Seed parent.*—"Charles Mallerin."

*Pollen parent.*—An unnamed seedling of "Charles Mallerin" × "Chrysler Imperial."

Propagation: Holds its distinguishing characteristics through succeeding propagations by budding.

*Flower*

Locality where grown and observed: Scappoose, Oregon.

Flowers borne: Usually singly; on very long and very strong stems.

Quantity of bloom: Abundant, outdoors.

Continuity: Continuous during growing season, but may begin somewhat late.

Fragrance: Moderate. Nature—Fruity.

Bud:

*Peduncle.*—Medium length (from 5.5 cm. to 7.5 cm.); medium heavy (from 3 mm. to 4 mm.); erect; few glandular cilia and several small red thorns. Color—near Brilliant Yellow Green, Plate 5 GY 8/8 (Nickerson), variably flushed with Dark Red, Plate 2.5 R 3/7 (Nickerson).

*Before calyx breaks.*—Size—medium (about 1.5 cm. x 2.5 cm., excluding receptacle). Form—Short pointed; with conspicuous neck; with irregular foliaceous appendages on lateral margins of some (usually alternate) sepals, with sometimes as many as three on one margin; with much-cut foliaceous parts extending beyond the tip of the bud, usually more than ½ the length of the bud, and in some cases, these are much expanded. Color—Strong Yellow Green, Plate 7.5 GY 7/9 (Nickerson), variably flushed with near Dark Red, Plate 2.5 R 3/7 (Nickerson).

*As calyx breaks.*—Color—near Deep Purplish Red, Plate 10RP 3/10 (Nickerson).

*As first petal opens.*—Size—medium. Form—from short pointed to near ovoid. Color: outer surface—between Rose Red, Plate 724, page 158 (Wilson) and Tyrian Purple, Plate 727, page 159 (Wilson), with base near Dresden Yellow, Plate 64/2, page 64 (Wilson); inner surface—near Rose Red, Plate 724, page 158 (Wilson), but slightly darker and more blue, with basal mark near Dresden Yellow, Plate 64/2, page 64 (Wilson).

Bloom:

*Size.*—Medium large (from 10 cm. to 13 cm.).

*Petalage.*—Double; from 30 to 35 petals; arranged quite regularly.

*Form.*—High-centered to cupped at first, but becoming cupped at maturity, with outer petals turned back toward stem; petals being at first loosely cupped inward, but later becoming rolled outward at apical lateral edges.

Petals:

*Texture.*—Medium thick; moderately soft. Inside—velvety. Outside—satiny.

*Shape.*—Outer petal—nearly round (about 5.7 cm. x 5.7 cm.); apical margin irregular, but without distinct notches. Intermediate petal — from obovate to broadly obovate (about 4.5 cm. x 5.3 cm.); apical margin irregular, but without distinct notches. Inner petal—obovate (about 4 cm. x 3 cm.); apical margin rough, but without distinct notches.

This description of a newly opened flower was made from a rose grown outdoors in the month of September at Scappoose, Oregon:

*Color.*—Outer petal: outside surface—between Rose Red, Plate 724, page 158 (Wilson) and Tyrian Purple, Plate 727, page 159 (Wilson), with base mark near Dresden Yellow, Plate 64/2, page 64 (Wilson), flushed slightly upward; inside surface—near Rose Red, Plate 724, page 158 (Wilson), with basal mark near Dresden Yellow, Plate 64/2, page 64 (Wilson). Intermediate petal: outside surface—between Rose Red, Plate 724, page 158 (Wilson) and Tyrian Purple, Plate 727, page 159 (Wilson), with base mark near Dresden Yellow, Plate 64/2, page 64 (Wilson), flushed slightly upward; inside surface—near Rose Red, Plate 724, page 158 (Wilson), with basal mark near Dresden Yellow, Plate 64/2, page 64 (Wilson). Inner petal: outside surface—slightly less blue than between Rose Red, Plate 724, page 158 (Wilson) and Tyrian Purple, Plate 727, page 159 (Wilson), with base mark near Dresden Yellow, Plate 64/2, page 64 (Wilson), flushed slightly upward; inside surface—slightly less blue than near Rose Red, Plate 724, page 158 (Wilson), with basal mark near Dresden Yellow, Plate 64/2, page 64 (Wilson).

This description was made from a rose that was open for 3 days outdoors in the month of September, at Scappoose, Oregon:

*Color.*—Outer petal: outside surface—slightly more blue than near Tyrian Purple, Plate 727/1, page 159 (Wilson), with basal mark near Dresden Yellow, Plate 64/3, page 64 (Wilson); inside surface—near Tyrian Purple, Plate 727, page 159 (Wilson), but flushed darker and bluer between veins, near Garnet Lake, Plate 828/3, page 172 (Wilson), with basal mark near Dresden Yellow, Plate 64/3 (Wilson). Intermediate petal: outside surface—between Tyrian Purple, Plate 727/2, page 159 (Wilson) and Rose Red, Plate 724/2, page 158 (Wilson), with basal mark near Dresden Yellow, Plate 64/2, page 64 (Wilson); inside surface—between Tyrian Purple, Plate 727/1, page 159 (Wilson) and Rose Red, Plate 724/1, page 158 (Wilson), with basal mark near Dresden Yellow, Plate 64/2, page 64 (Wilson). Inner petal: outside surface—between Tyrian Purple, Plate 727, page 159 (Wilson) and Rose Red, Plate 724, page 158 (Wilson), with basal mark near Dresden Yellow, Plate 64/2, page 64 (Wilson); inside surface—between Tyrian Purple, Plate 727, page 159 (Wilson) and Rose Red, Plate 724, page 158, (Wilson), but closer to latter, with basal mark near Dresden Yellow, Plate 64/2, page 64 (Wilson).

*General color effect.*—Newly opened flower—Rose Red, Plate 724, page 158 (Wilson). 3-days open—near Tyrian Purple, Plate 727/1, page 159 (Wilson).

*Behavior.*—Petals drop off cleanly; color becomes somewhat more blue during senescence; color is unusually stable in hot, dry, bright weather; during cool weather and particularly in the latter part of the season, the general color becomes more blue and darker, and this is especially noted in the outside petals, which may be a deep dark velvety red-purple, possibly related to Red-Purple, Plate 7.5 (Nickerson), but much deeper.

*Flower longevity.*—On bush in garden—4 days in August. Cut roses grown outdoors and kept at living-room temperatures—3 days in August.

*Reproductive organs*

Stamens: Moderately numerous; arranged quite regularly about pistils on margin of receptacle immediately adjacent to petal base.

Filaments: Medium long (about 8 mm. to 11 mm.); almost all with anthers. Color—variable; near Strong Red, Plate 2.5 R 5/12 (Nickerson).

Anthers: Medium size (about 1 mm. x 3 mm.); open approximately at the same time. Color—near Moderate Orange Yellow, Plate 7.5 YR 8/8 (Nickerson).

Pollen: Abundant. Color—Dark Yellow.

Pistils: Moderately numerous.

Styles: Slightly contorted; somewhat uneven; shorter in center of column; medium thin; medium length (about 7 mm.); bunched, but free.

Stigma: Ordinary.

Ovaries: Outer overies exposed above receptacle, with cottony tissue surrounding.

Hips: Globular; slightly obovate; without conspicuous neck; quite smooth; walls medium thick and fleshy; do not develop readily. Color (mature—variable; orange.

Sepals: Persistent; long (about 4 cm.); with large apical foliaceous expansion common; nearly straight edges; slightly recurved.

Seeds: Few; medium size.

*Plant*

Foliage:

*Leaves.*—Usually 7 leaflets, but sometimes 5; abundant; medium large (about 7 cm. x 3.8 cm.); heavy; semi-glossy; smooth.

*Leaflets.*—Ovate, with apex from acute to acuminate. Base—rounded. Margin — simply irregularly serrate.

*Color.*—Mature: upper surface—between Varley's Green, 31'.Y–G m, Plate XVIII (Ridgway) and Dark Dull Yellow Green, 31".Y–Gm, Plate XXXII (Ridgway); under surface—near Bice Green, 29'.GG–Y.k, Plate XVII (Ridgway). Young: upper surface—near Burnt Lake, 71.V–RR.m, Plate XII (Ridgway), but darker and more brown; under surface—near Perilla Purple, 65".RR–V.k, Plate XXXVII (Ridgway).

*Rachis (the supporting stem of the compound leaf).*—Heavy. Upper surface of groove—hairy; lateral ridges with several glandular cilia. Under surface—very few thorns; few glandular cilia.

*Stipules.*—Medium size (about 8 mm. x 15 mm.); with medium length points (about 4 or 5 mm.) turning out at an angle of less than 45°.

*Disease resistance.*—Ordinary resistance to mildew, as determined by field observation in comparison with other varieties grown under comparable cultural conditions at Scappoose, Oregon.

Growth:

*Habit.*—Upright; bushy; moderately branched.

*Growth.*—Free.

*Canes.*—Medium heavy.

*Main stems.*—Color—near Asphodel Green, 29'''. GG–Y., Plate XLI (Ridgway). Thorns—numerous; medium long (about 1.5 cm.); almost straight, but with slight downward tilt; base medium oval (about 5 mm. x 10 mm.); color—brown. Prickles—from very few to none. Hairs—none.

*Branches.*—Color—near Shamrock Green, 33".GY–G.i, Plate XXXII (Ridgway). Thorns—numerous; medium long (about 1.0 cm.), with slight downward hook; base medium oval (about 4 mm. x 9 mm.); color—light reddish brown. Prickles—very few, but usually none. Hairs—none.

*New shoots.*—Color—near Indian Purple, 67".V-R.m, Plate XXXVIII (Ridgway), gradually becoming green. Thorns—numerous; small; slightly hooked downward; base medium oval; color—reddish. Prickles—several; often glandular; color—reddish. Hairs—few gland-tipped cilia near base of shoot.

I claim:

A new and distinct variety of rose plant of the hybrid tea class, substantially as herein shown and described, characterized particularly as to novelty by the unique combination of an upright, bushy, vigorous, medium tall plant habit, abundant, large and well-distributed foliage of a deep green color, a continuous and quite floriferous flowering habit throughout the growing season, a habit of bearing flowers singly on long, strong stems, a unique combination of flower form and color, and a tendency for one or more axial buds to begin growth before the flower reaches senescence.

No references cited.

Feb. 23, 1960 G. J. VON ABRAMS Plant Pat. 1,914
ROSE PLANT
Filed Jan. 9, 1959
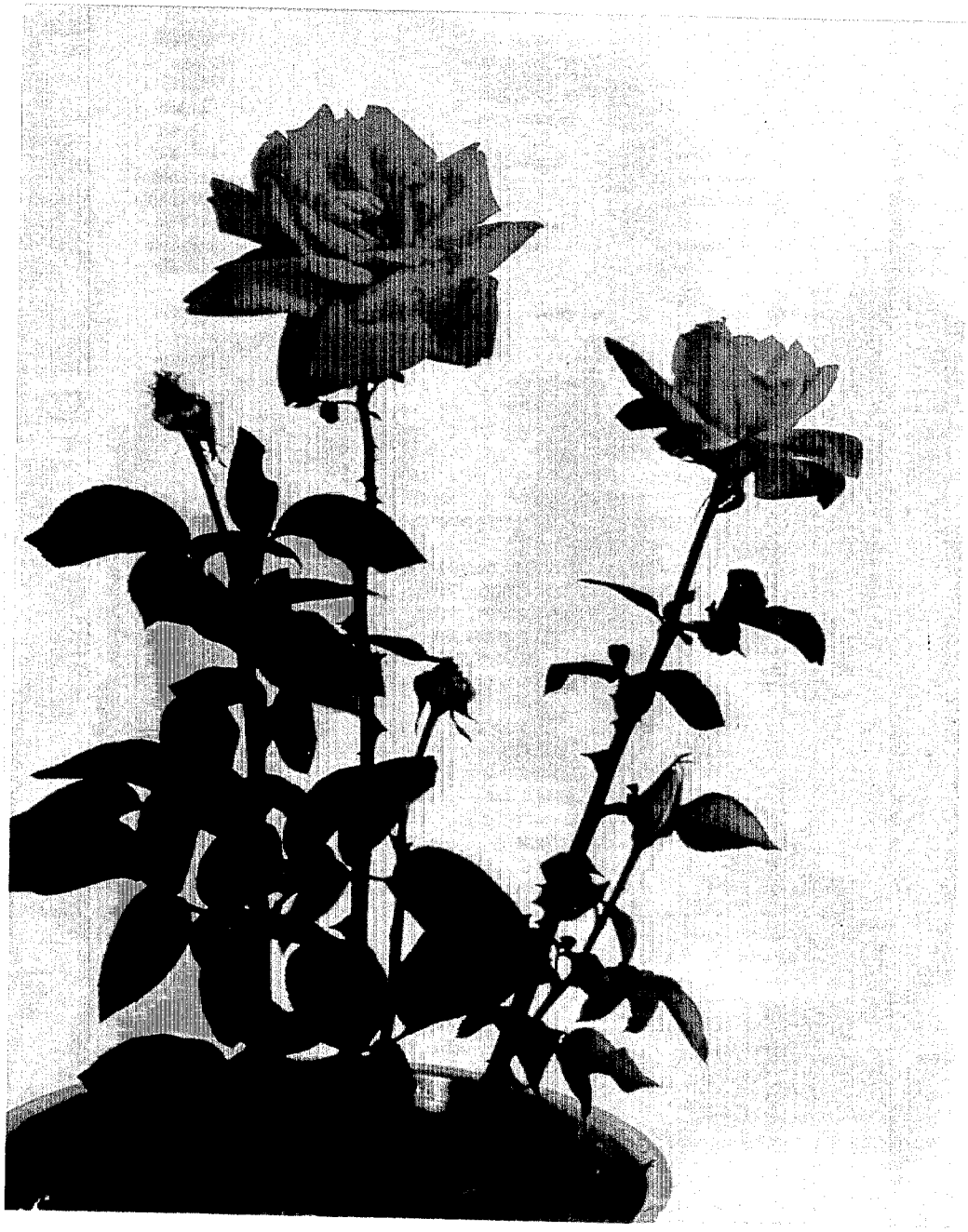
Inventor.
G. J. von Abrams
By: Robb & Robb
Attorneys.